United States Patent [19]

King et al.

[11] Patent Number: 5,270,923

[45] Date of Patent: * Dec. 14, 1993

[54] COMPUTED TOMOGRAPHIC IMAGE RECONSTRUCTION METHOD FOR HELICAL SCANNING USING INTERPOLATION OF PARTIAL SCANS FOR IMAGE CONSTRUCTION

[75] Inventors: Kevin F. King, New Berlin; Albert H. R. Lonn, Waukesha; Carl R. Crawford, Milwaukee, all of Wis.

[73] Assignee: General Electric Company, Milwaukee, Wis.

[*] Notice: The portion of the term of this patent subsequent to Aug. 3, 2010 has been disclaimed.

[21] Appl. No.: 430,372

[22] Filed: Nov. 2, 1989

[51] Int. Cl.$^5$ ............................................. G06F 15/42
[52] U.S. Cl. ............................................. 364/413.13
[58] Field of Search ...................... 364/413.16, 413.17, 364/413.19

[56] References Cited

U.S. PATENT DOCUMENTS

| | | | |
|---|---|---|---|
| 4,284,896 | 8/1981 | Stonestrom | 364/413.18 |
| 4,630,202 | 12/1986 | Mori | 364/413.15 |
| 4,789,929 | 12/1988 | Nishimura et al. | 364/413.15 |

*Primary Examiner*—Gail O. Hayes
*Attorney, Agent, or Firm*—Quarles & Brady

[57] ABSTRACT

A method of reducing image artifacts in images acquired with fan beam, helical scanning, tomographic imaging systems uses half scans of less than 360° of projection data of an imaged object on each side of the slice plane being imaged. The half scans are weighted with half scan weighting factors to compensate for redundant data and are weighted with helical scanning weighting factors to interpolate the half scans projection data to projection data at the slice plane. The imaged object may be moved one slice thickness for each 360° of scanning so that the half scans are concentrated closer to the slice plane thereby reducing interpolation errors. Alternatively, for a series of slice images, the imaged object may be moved one slice thickness for each half scan to reduce average slice acquisition time.

12 Claims, 6 Drawing Sheets

COMPUTED TOMOGRAPHIC IMAGE RECONSTRUCTION METHOD FOR HELICAL SCANNING USING INTERPOLATION OF PARTIAL SCANS FOR IMAGE CONSTRUCTION

BACKGROUND OF THE INVENTION

This invention relates to computed tomography using helical scanning. More specifically, the invention relates to an image reconstruction method for reducing image artifacts that result from acquiring tomographic projection data in a helical scan.

As used herein, computed tomography shall refer to both tomography using "transmission imaging" that is, detecting radiation transmitted through the body being imaged, and "emission imaging", detecting radiation emitted from the body being imaged, e.g., such as that being emitted by radiopharmaceutical isotopes.

In a transmission imaging computed tomography system, an x-ray source is collimated to form a fan beam with a defined fan beam angle. The fan beam is orientated to lie within the x-y plane of a Cartesian coordinate system, termed the "imaging plane", and to be transmitted through an imaged object to an x-ray detector array orientated within the imaging plane. The detector array is comprised of detector elements which each measure the intensity of transmitted radiation along a ray projected from the x-ray source to that particular detector element. The detector elements can be organized along an arc each to intercept x-rays from the x-ray source along a different ray of the fan beam. The intensity of the transmitted radiation is dependent on the attenuation of the x-ray beam along the ray by the imaged object.

The x-ray source and detector array may be rotated on a gantry within the imaging plane, around the imaged object, so that the fan beam intercepts the imaged object at different angles. At each angle, a projection is acquired comprised of the intensity signals from each of detector elements. The gantry is then rotated to a new angle and the process is repeated to collect a number of projections at different angles to form a tomographic projection set.

The acquired tomographic projection set is typically stored in numerical form for computer processing to "reconstruct" a slice image according reconstruction algorithms known in the art. The reconstructed slice images may be displayed on a conventional CRT tube or may be converted to a film record by means of a computer controlled camera.

In either emission or transmission computed tomography the detector array may be rectilinear rather than arcuate.

A typical computed tomographic study entails the imaging of a series of slices of an imaged object with the slices displaced incrementally along a z-axis perpendicular to the x and y axes, so as to provide a third spatial dimension of information. A radiologist may visualize this third dimension by viewing the slice images in order of position along the z-axis, or the numerical data comprising the set of reconstructed slices may be compiled by computer programs to produce shaded, perspective representations of the imaged object in three dimensions.

As the resolving power of computed tomography methods increases, additional slices are required in the z-dimension. The time and expense of a tomographic study increases with the number of slices required. Also, longer scan times increase the discomfort to the patient who must remain nearly motionless to preserve the fidelity of the tomographic reconstructions. Accordingly, there is considerable interest in reducing the time required to obtain a slice series.

The time required to collect the data for a series of slices depends in part on four components: a) the time required to accelerate the gantry to scanning speed, b) the time required to obtain a complete tomographic projection set, c) the time required to decelerate the gantry and d) the time required to reposition the patient in the z-axis for the next slice. Reducing the time required to obtain a full slice series may be accomplished by reducing the time required to complete any of these four steps.

The time required for acceleration and deceleration of the gantry may be avoided in tomographic systems that use slip rings rather than cables to communicate with the gantry. The slip rings permit continuous rotation of the gantry. Hereafter, it will be assumed that the CT systems discussed are equipped with slip rings or the equivalent to permit continuous rotation of over 360°.

The time required to acquire the tomographic data set is more difficult to reduce. Present CT scanners require on the order of one to two seconds to acquire the projection set for one slice. This scan time may be reduced by rotating the gantry at a faster speed. A higher gantry speed, in general, will reduce the signal-to-noise ratio of the acquired data by the square root of the factor of rotational rate increase. This may be overcome to some extent in transmission tomography devices by increasing the radiation output of the x-ray tube, but is subject to the power limits of such devices.

A reduction in patient repositioning time may be accomplished by translating the patient in the z-axis synchronously with the rotation of the gantry. The combination of constant patient translation along the z-axis during the rotation of the gantry and acquisition of projection data has been termed "helical scanning" and refers to the apparent path of a point on the gantry with respect to a reference point on the imaged body. As used herein, "helical scanning" shall refer generally to the use of continuous translation of the patient or imaged object during the acquisition of tomographic imaging data, and "constant z-axis scanning" shall refer to the acquisition of the tomographic data set without translation of the patient or imaged object during the acquisition period.

Continuous translation of the imaged object during scanning shortens the total scanning time required for the acquisition of a given number of slices by eliminating the length of time normally required for repositioning the patient between scans. However, helical scanning introduces certain errors with regard to the data in the acquired tomographic projection sets. The mathematics of tomographic reconstruction assumes that the tomographic projection set is acquired along a constant z-axis slice plane. The helical scan path clearly deviates from this condition and this deviation results in image artifacts in the reconstructed slice image if there is any significant change in the object in the z-axis. The severity of the image artifacts depends generally on the "helix offset" in the projection data, measured as the difference between the table locations of the scanned data and the z axis value of the desired slice plane. Errors resulting from helical scanning will be referred to collectively as "skew" errors.

Several methods have been used to reduce skew errors in helical scanning. A first approach disclosed in U.S. Pat. No. 4,630,202 issued Dec. 16, 1986, reduces the pitch of the helical scan and then averages the projection data of consecutive 360° tomographic projection sets. The effect is equivalent to using a detector array with a larger width along the z axis, which also moves less in the z direction during rotation of the gantry, i.e. with a lesser scanning pitch. Skew errors are reduced using this method, but at the expense of additional scanning time necessitated by the lower scanning pitch. Thus, this method reduces, to some extent, the advantages to be gained by helical scanning.

Skew errors at the ends of the tomographic projection set may be reduced in conjunction with this approach by changing the weighting of the last and first projections of the consecutive 360° tomographic projection sets in the "averaging" process to give greater weight to the projection closest to the slice plane.

A second approach disclosed in U.S. Pat. No. 4,789,929 issued Dec. 6, 1988, also applies weighting to the projections of combined, consecutive 360° tomographic projection sets, but the weighting is a function of the helical offset of each projection at the given gantry angle. This approach of interpolating over 720° generally increases partial volume artifacts. Partial volume artifacts are image artifacts arising when certain volume elements of the imaged object contribute to only some of the projections of the projection set.

A third approach, described in copending U.S. Pat. No. 5,046,003 entitled: "Method for Reducing Skew Image Artifacts in Helical Projection Scanning" and assigned to the same assignee as the present invention, uses non-uniform table motion to concentrate the helically acquired projections near the slice plane while limiting the accelerative forces on the patient.

SUMMARY OF THE INVENTION

It is understood in the art, that a tomographic image may be prepared from less than 360° of projection data. Generally, this result arises from the equivalence in attenuation of certain rays in projection acquired at gantry angles 180° apart. The method of reconstructing a tomographic image from less than 360° of data is termed "half scan" and requires that the acquired data be weighted by a "half scan weighting function" prior to reconstruction of the image.

The present invention reduces skew artifacts by interpolating between two or more half scan tomographic projection sets comprised of less than 360° of projection data as opposed to full scan tomographic image sets comprised of 360° of projection data. A first and second half scan of projection data is acquired on either side of a slice plane and a half scan weighting function is applied to this data. A helical scan weighting function is also applied to this data and the combined first and second data sets, as weighted, are reconstructed into a slice image.

It is one object of the invention to permit the acquisition of projection data, for an interpolated tomographic projection set, over a shorter z-axis distance. For a given scan pitch, the use of half scans rather than full scans requires less z-axis travel in a helical scan. This in turn concentrates the projections acquired at points closer to the slice plane and thus improves the accuracy of the interpolation and decreases partial volume artifacts.

It is another object of the invention to permit the acquisition of projection data, for an interpolated tomographic projection set, over a shorter time period. Image artifacts may result from patient motion during the acquisition of the projection data of a tomographic projection set. For a given gantry speed, the use of half scans rather than full scans permits the acquisition of the necessary data in less time. This in turn can reduce patient-motion induced partial volume artifacts.

It is yet another object of the invention to permit a series of slice images to be acquired in less time. The scanning pitch may be increased so that the distance between slice planes corresponds to the gantry rotation required to acquire a half scan rather than a full scan. For a given gantry speed, this will decrease the time required to acquire a series of slice plane images.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
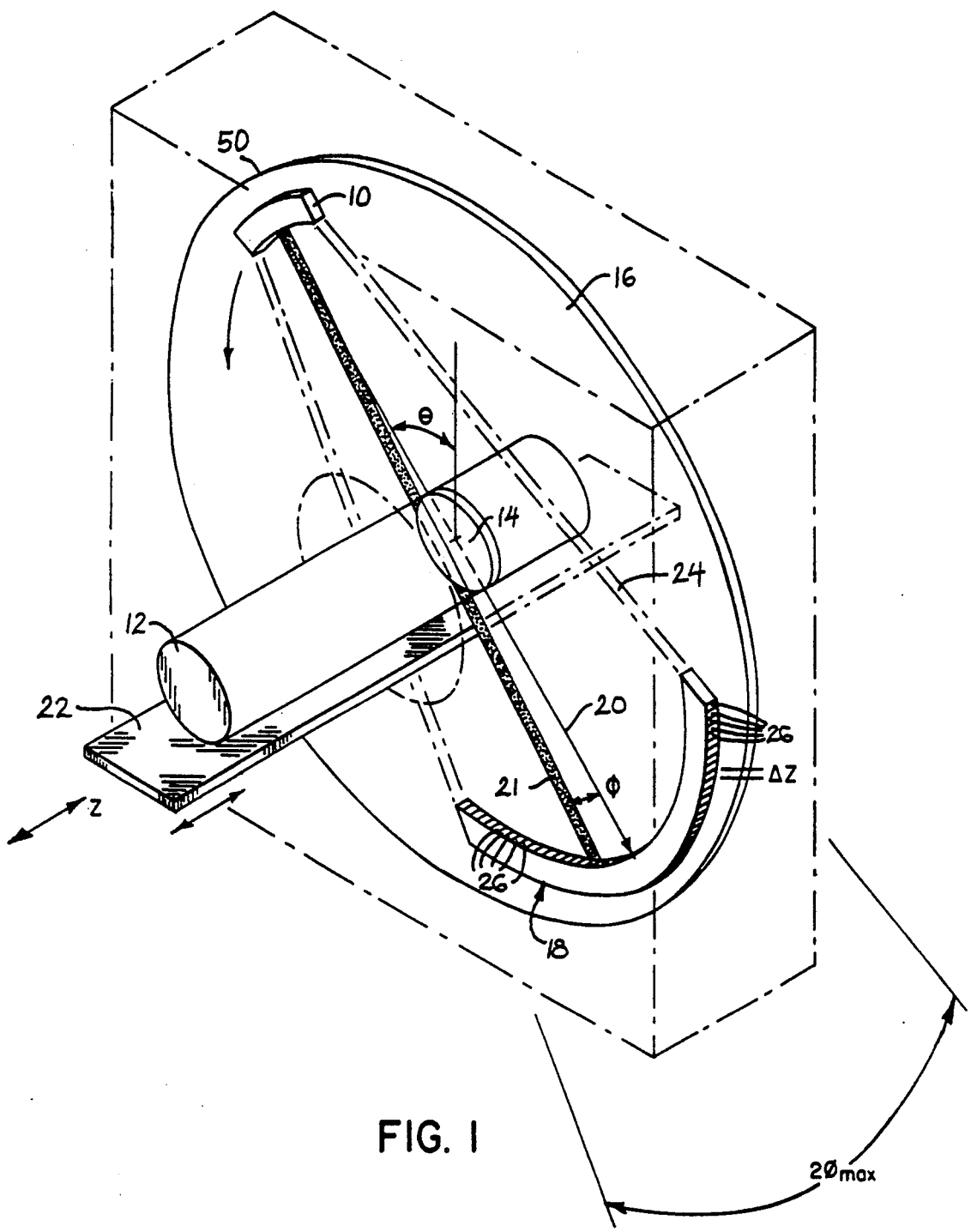
FIG. 1 is a pictorial representation of a CT apparatus including gantry, table and imaged object, and showing the relative angles and axes associated therewith.

Referring to FIG. 1, a CT gantry 16, representative of a "third generation" CT scanner includes an x-ray source 10 oriented to project a fan beam of x-rays 24 through imaged object 12 to detector array 18. The fan beam 24 is directed along an x-y plane of a Cartesian coordinate system, the "imaging plane", and subtends a "fan angle" of $2\phi_{max}$ as measured along the imaging plane. The detector array 18 is comprised of a number of detector elements 26 which together receive and detect a value proportional to the magnitude of a projected image resulting from the transmission of x-rays through the imaged object 12, or in the case of emission tomography, from the radiation emitted from the radiopharmaceutical isotopes within the imaged object 12. The angle $\phi$, measured from the centermost ray 20 of the fan beam 24, may identify each ray 21 of the fan beam 24 and its associated detector 26 and will be termed the fan beam angle.

The angular position $\theta$ of the gantry 16 with respect to the imaged object 12 is arbitrarily referenced to zero when the fan beam's center most ray 20 is vertical and directed downward. The gantry 16 is coupled to the gantry associated control modules 48, shown in FIG. 3 and to be described below, by means of slip rings 50 and is therefore free to rotate continuously through angles greater than 360° to acquire projection data.

The imaged object 12 rests on table 22 which is radiotranslucent so as not to interfere with the imaging process. Table 22 may be controlled so that its upper surface translates along the z axis perpendicular to the x-y imaging plane, by moving the imaged object 12 across the imaging plane swept by the fan beam 24. For simplicity, it will be assumed henceforth that the table 22 moves at a constant velocity and therefore that the z axis position of the table 22 is proportional to the angular position $\theta$ of the gantry 16. Accordingly, the tomographic projections acquired may be defined either in terms of z or $\theta$.

Figure 2A:
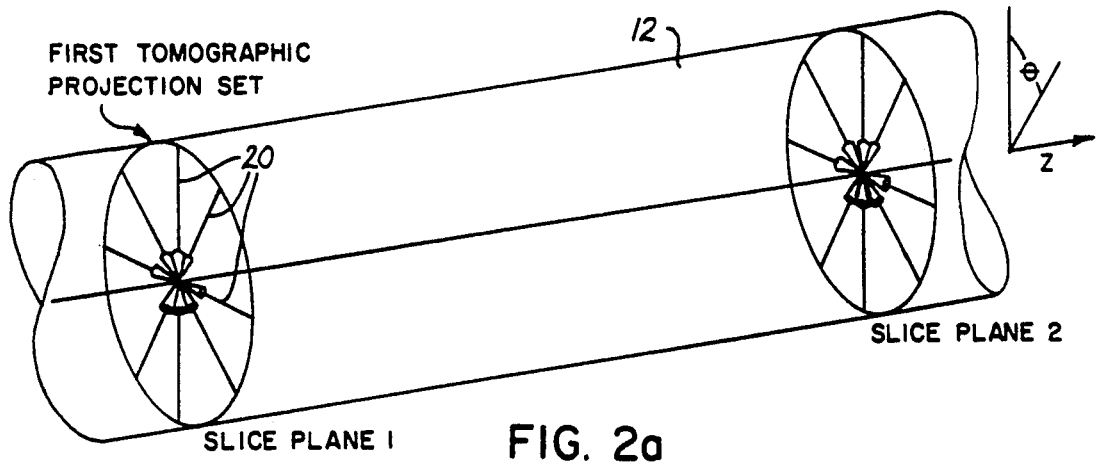
FIG. 2(a) and 2(b) are schematic illustrations of the imaged object of FIG. 1 showing the relative orientation of the gantry and imaging plane with respect to the imaged object for constant z axis scanning and helical scanning respectively. The pitch of the helical scanning is exaggerated for clarity.
Figure 2B:
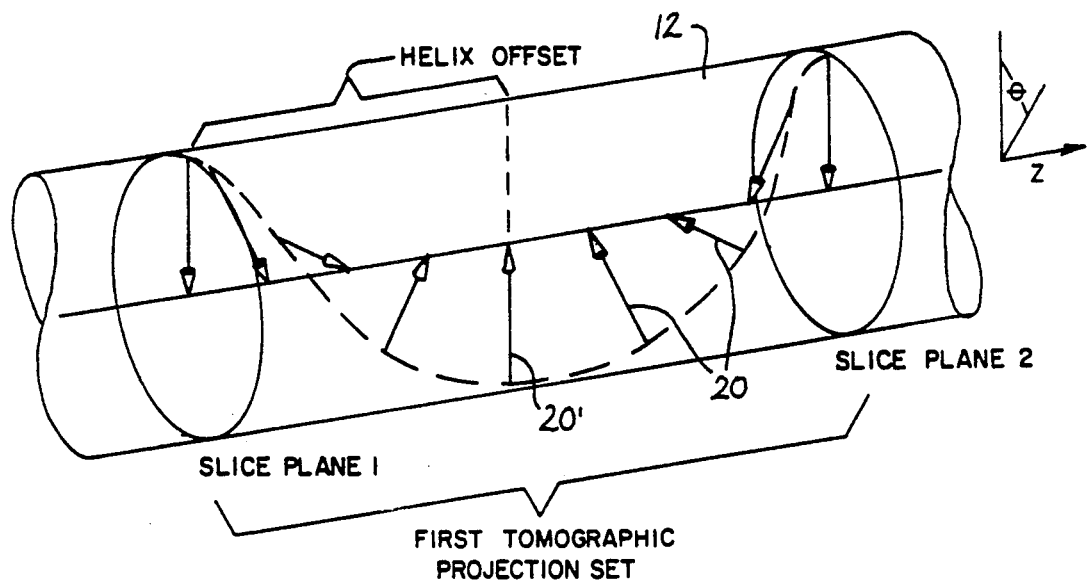

Referring to FIGS. 2(a) and 2(b), the angular position of the gantry and the z-axis position of the imaging plane with respect to the imaged object is shown by projection arrows 20 for a constant z-axis scan and a helical scan, respectively. In the constant z-axis scan, shown in FIG. 2(a) each tomographic projection set is acquired at a constant z-axis position and the imaged object is moved along the z-axis to the next slice plane between such acquisitions.

This differs from the helical scan in FIG. 2(b) where the z-axis position of the imaged object with respect to the imaging plane changes constantly during the acquisition of each tomographic projection set. Accordingly, arrows 20 trace a helix within the imaged object along the z-axis. The pitch of the helix will be referred to as the scanning pitch.

Figure 3:
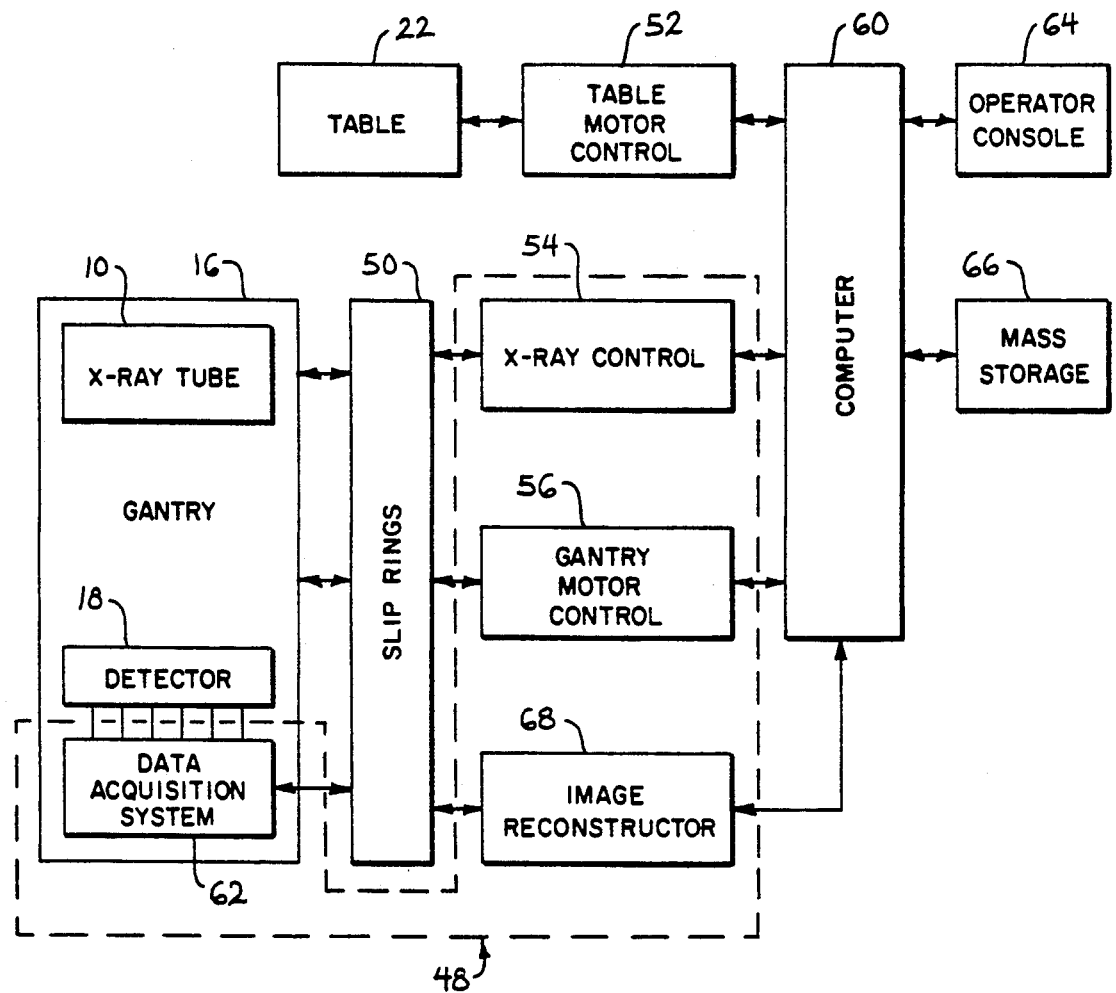
FIG. 3 is a block diagram of a CT control system that may be used with the CT apparatus of FIG. 1, and that is useful for practicing the present invention.

Referring now to FIG. 3, the control system of a CT imaging system suitable for use with the present invention has gantry associated control modules 48 which include: x-ray control 54 which provides power and timing signals to the x-ray source 10, gantry motor controller 56 which controls the rotational speed and position of the gantry 16 and provides information to computer 60, and data acquisition system 62, regarding gantry position, and image reconstructor 68 which receives sample and digitized signals from the detector array 18 via the data acquisition system 62 to perform high speed image reconstruction according to methods known in the art. Each of the above can be connected to its associated elements on the gantry 16 via slip rings 50 and serves to interface computer 60 to various gantry functions.

The speed and position of table 22 along the z-axis, is communicated to and controlled by computer 60 by means of table motor controller 52. The computer 60 receives commands and scanning parameters via operator console 64 which is generally a CRT display and keyboard which allows the operator to enter parameters for the scan and to display the reconstructed image and other information from the computer 60. A mass storage device 66 provides a means for storing operating programs for the CT imaging system, as well as image data for future reference by the operator.

In conventional CT imaging, 360° of projection data, a full tomographic projection set, is acquired and reconstructed into a slice image. Alternatively, a tomographically reconstructed image may be derived from projection data acquired over less than 360° of gantry 16 rotation provided at least a minimum gantry rotation of 180° plus the fan beam angle is obtained. Image reconstruction using less than 360° of projection data will be termed "half scan" to distinguished it from "full scan" image reconstruction which requires 360° of projection data. The data used to reconstruct a half scan image will be termed a "half scan data set".

As a result of the fan beam geometry of the x-ray source 10 and the detector array 18, to be discussed further below, a half scan will contain certain redundant data. This redundant data requires that the half scan data set be weighted with a "half scan weighting" function so that the redundant data does not make a disproportionate contribution to the final image when incorporated with the non-redundant data. The weighting and reconstruction of images from a half scan data set are discussed in detail in "Optimal Short Scan Convolution Reconstruction for Fanbeam CT", Dennis L. Parker, Medical Physics 9(2) March/April 1982.

Figure 4:
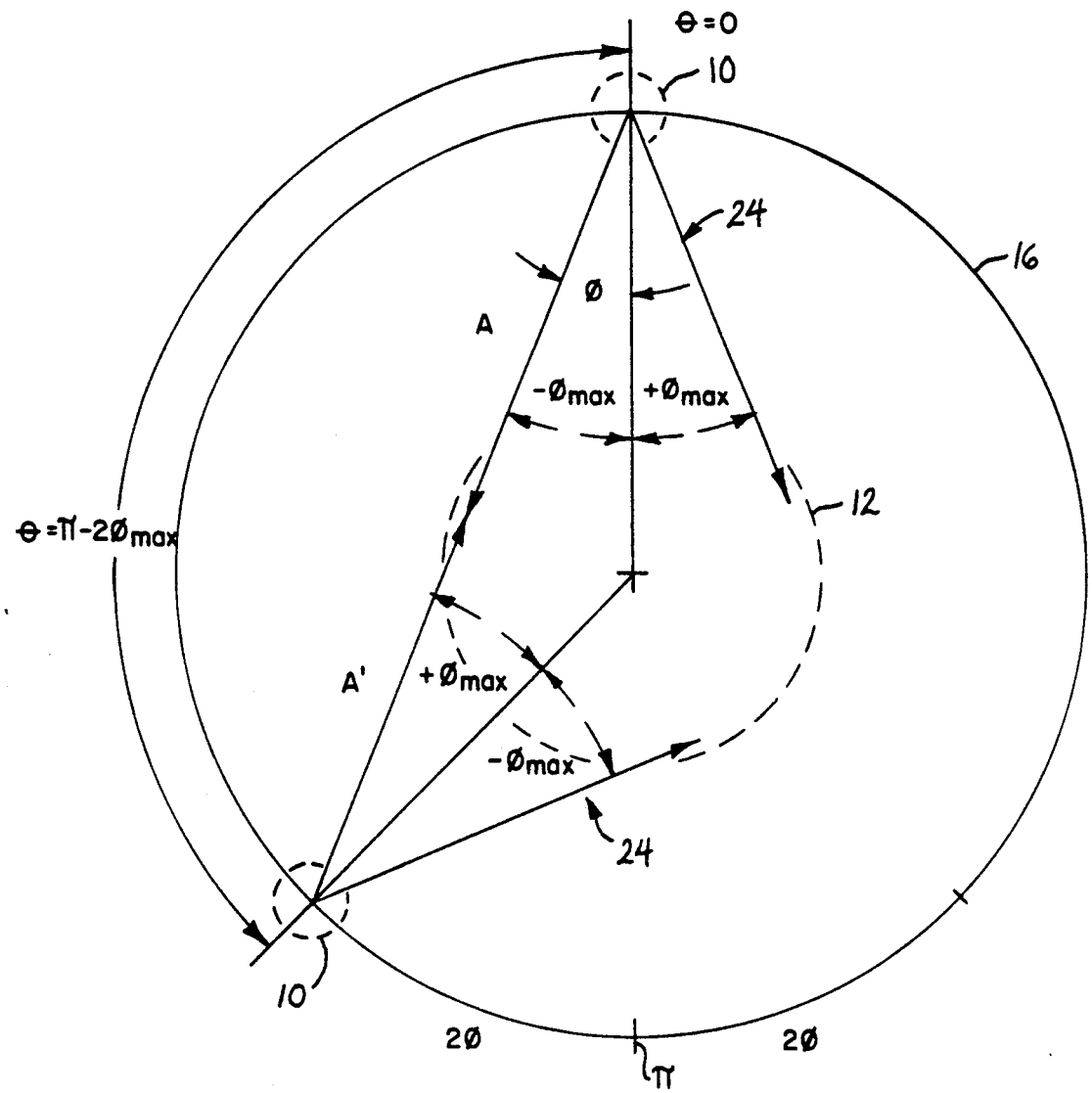
FIG. 4 is a diagram showing the geometry of an x-ray fan beam produced by the CT apparatus of FIG. 1 with the gantry shown positioned at two gantry angles $\theta$ as viewed along the z-axis.

The source of the redundant data within a half scan acquired with a fan beam geometry may be demonstrated graphically. Referring to FIG. 4, a fan beam 24 at first gantry position $\theta=0$ includes ray A at angle $-\phi_{max}$ within the fan beam 24. The ray A is received by a detector element 26 (not shown) which produces a signal $P(\theta_1, -\phi_{max})$, where $\theta_1=0$, proportional to the line integral of the absorption of the x-ray radiation along ray A by imaged object 12. At a second fan beam 24 at second gantry position $\theta_2=\pi-2\phi_{max}$, it will be appreciated that the same line integral absorption measured along ray A in the first gantry position, is also measured along ray A' in the second gantry position, where ray A' is at angle $+\phi_{max}$ within the fan beam 24. The x-ray along ray A' is received by a detector element 26 (not shown) which produces a signal $P(\theta_2, \phi_{max})$. The identity of the measurements along ray A and A' may be generalized by the following relationship:

$$P(\theta, \phi) = P(\theta + \pi + 2\phi, -\phi) \tag{1}$$

where $\theta$ and $\phi$ are any gantry angle and any fan beam angle respectively.

Figure 5:
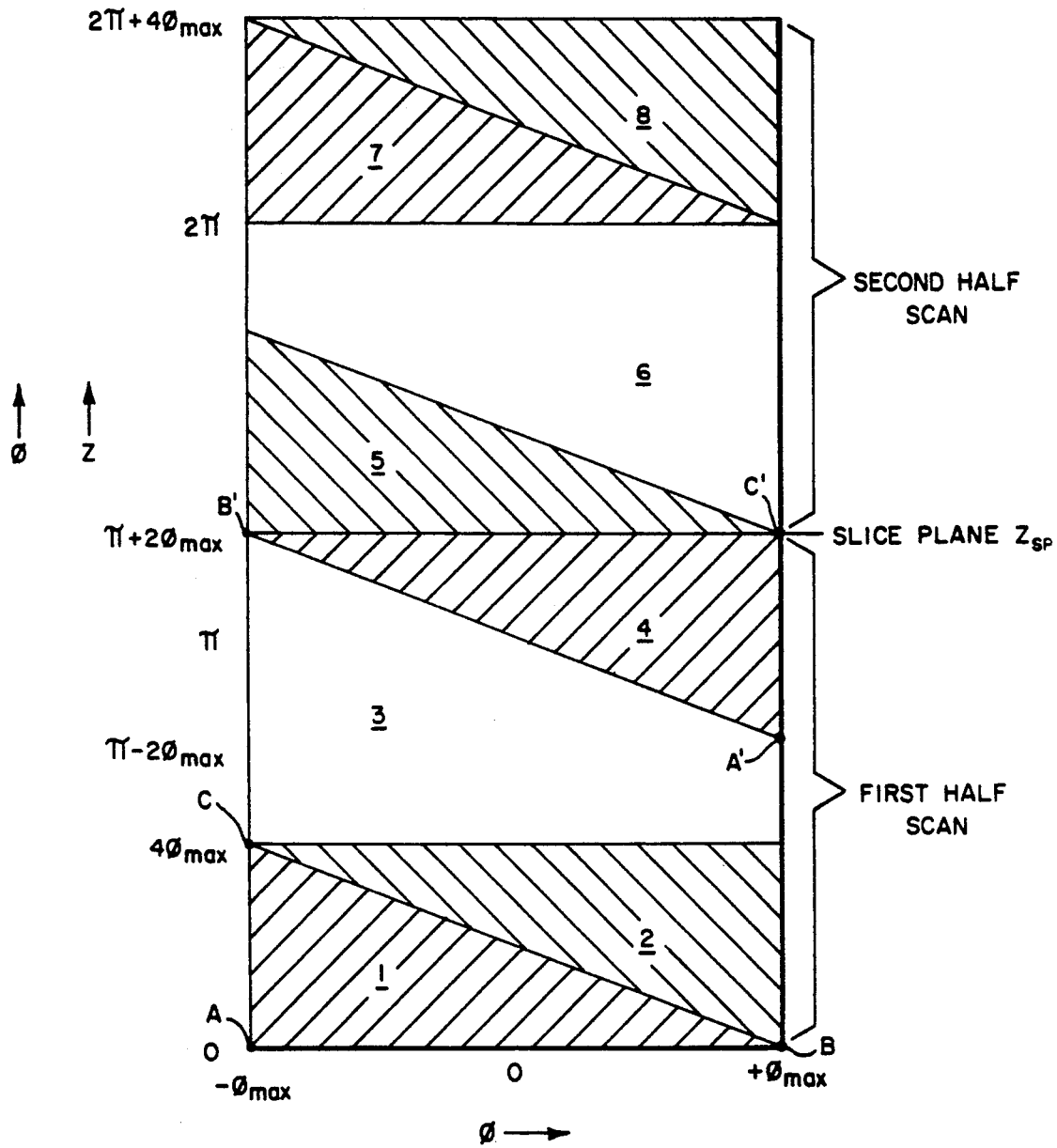
FIG. 5 is a graphical representation of the arguments $\theta$ and $\phi$ associated with the projection data of two half scans acquired in a helical scan with the CT apparatus of FIG. 1.

In the present invention, two consecutive half scans of tomographic data are acquired over a gantry 16 rotation 360° plus twice the fan beam angle, $2\phi_{max}$. During the acquisition of these half scans, the table 22 and hence the imaged object 12 are advanced along the z-axis. Referring to FIG. 5, the arguments $\theta$ and $\phi$ for data for this first and second half scan are shown schematically. Lines parallel to AB represent projections taken at gantry position $\theta$ and includes detector signals from angles $\phi$: $-\phi_{max} < \phi < +\phi_{max}$. The gantry angle $\theta$ of the projection along line AB is arbitrarily assigned to 0 and is the first projection of the first half scan. Successive projections are acquired at increasing gantry angles $\theta$ up to $\theta = \pi + 2\phi_{max}$ radians while the table 22 is advanced along the z-axis, per helical scanning techniques discussed above.

When the gantry angle reaches $\theta = \pi + 2\phi_{max}$ radians, the first half scan is complete and the slice plane $z_{sp}$ of the imaged object 12 has been aligned with the imaging plane. A second half scan is then initiated starting at gantry angle $\theta = \pi + 2\phi_{max}$ and continuing to gantry angle $\theta = 2\pi + 4\phi_{max}$.

As mentioned, each half scan must contain at least $\pi + 2\phi_{max}$ radians of projections in order to reconstruct a full tomographic projection set. Nevertheless, as a result of the geometry of scanning, each half scan contains some projections with "duplicative" rays per equation 1. For example, the rays of projections in triangular zone "1" at the start of the first half scan, as shown in FIG. 5, are equivalent, per equation 1, to the rays in triangular zone "4" at the end of the first half scan. Note, however, that unlike the case of constant z-axis scanning, the data in zone "4" does not necessarily have same values as the corresponding data in zone "1" because the imaged object 12 has been displaced along the z axis between the zone measurements because of the helical scanning. The term "redundant data" will be used to refer to this data within each half scan whose rays are related by equation 1 even though the values of the data may differ as a result of the helical scanning.

Referring again to FIG. 5, in the present invention, the data in each of two consecutive half scans is interpolated to the slice plane. Accordingly, two sets of weighting factors must be considered: an interpolation weight and a half scan weight. The weighting used for interpolation will be termed the "helical weighting function" to distinguish it from the "half scan weighting function" applied to the redundant data within each half scan.

For convenience of discussion, the following zones, as shown in FIG. 5, are defined with respect to a slice plane positioned at the image plane when the gantry is at $\theta = \pi + 2\phi_{max}$.

| ZONE | BOUNDARIES |
|---|---|
| 1 | $0 < \theta < 2\phi_{max} - 2\phi$ |
| 2 | $2\phi_{max} - 2\phi < \theta < 4\phi_{max}$ |
| 3 | $4\phi_{max} < \theta < \pi - 2\phi$ |
| 4 | $\pi - 2\phi < \theta < \pi + 2\phi_{max}$ |
| 5 | $\pi + 2\phi_{max} < \theta < \pi + 4\phi_{max} - 2\phi$ |
| 6 | $\pi + 4\phi_{max} - 2\phi < \theta < 2\pi$ |
| 7 | $2\pi < \theta < 2\pi + 2\phi_{max} - 2\phi$ |
| 8 | $2\pi + 2\phi_{max} - 2\phi < \theta < 2\pi + 4\phi_{max}$ |

These zones distinguish areas of redundant data within each half scan and "complementary" data between half scans. Complementary data is data in one half scan that is equivalent per equation 1, to data in the other half scan on the opposite side of the slice plane.

Zones 1 and 4 are redundant per equation 1, and zones 1 and 4 are each complementary with zone 7 per equation 1. Likewise, zones 5 and 8 are redundant, and complementary with zone 2, and zones 3 and 6 are complementary.

For interpolation, the helical scan weights must be chosen to combine each zone with another complementary zone on the opposite side of the slice plane a $\pi + 2\phi_{max}$. For example, zone 1 must be combined with zone 7 to effectively interpolate data to the slice plane. Zone 1 is not combined with zone 4 because they are both on the same side of the slice plane. Similarly, zone 3 is combined with zone 6. Zone 2 could be combined with either zone 5 or zone 8 since both are on opposite sides of the slice plane. When both combinations are used, however, zone 2 will receive disproportionate weighting in the reconstruction. Therefore two helical scanning weights are assigned to zone 2, corresponding to zones 5 and 8, and the weight of the zone is later adjusted by the half scan weights to be described below.

Continuing this progression, zone 4 is combined with zone 7. Zone 7 must also be combined with zone 1 and therefore requires two sets of helical scan weights. Again, the effect of these two combinations of zone 7 is accounted for in the half scan weights described in detail below.

After the application of these weights, the combined first and second half scan may be reconstructed directly into an image interpolated to the slice plane by operation on the combined data set of 180° plus the fan beam angle. Alternatively, because of the linearity of the reconstruction process, the helical scan weights and half scan weights may be applied and the two half scans may be reconstructed directly as 360° plus twice the fan beam angle of projection data, as is known in the art.

The total weighting for each zone, as mentioned, will be a combination of helical scan weights and half scan weights. The helical scan weights for each zone will be a function of $\theta$ and $\phi$ and denoted $he_{i,j}$, where i is the zone number of the data being weighted and j is the zone number of the other data in the complementary zone. The half scan weights for each zone also will be a function of $\theta$ and $\phi$ and denoted $ha_{i,j}$, where i is the zone number of the data being weighted and j is the zone number of the other data in the complementary zone. With this convention, the total weight applied to each zone will be:

| ZONE | TOTAL WEIGHT |
|---|---|
| 1 | $(ha_{1,7} \cdot he_{1,7})$ |
| 2 | $(ha_{2,5} \cdot he_{2,5}) + (ha_{2,8} \cdot he_{2,8})$ |
| 3 | $(ha_{3,6} \cdot he_{3,6})$ |
| 4 | $(ha_{4,7} \cdot he_{4,7})$ |
| 5 | $(ha_{5,2} \cdot he_{5,2})$ |
| 6 | $(ha_{6,3} \cdot he_{6,3})$ |
| 7 | $(ha_{7,4} \cdot he_{7,4}) + (ha_{7,1} \cdot he_{7,1})$ |
| 8 | $(ha_{8,2} \cdot he_{8,2})$ |

For a linear interpolation assuming the zones are combined as described above, the helical scan weights are functions of $\theta$ and $\phi$ as follows:

$$he_{1,7} = he_{2,8} = 1 + \frac{\theta - \theta_{sp}}{2\pi} \quad (2)$$

$$he_{2,5} = he_{3,6} = he_{4,7} = 1 + \frac{\theta - \theta_{sp}}{\pi + 2\phi} \quad (3)$$

$$he_{5,2} = he_{6,3} = he_{7,4} = 1 + \frac{\theta_{sp} - \theta}{\pi - 2\phi} \quad (4)$$

$$he_{7,1} = he_{8,2} = 1 + \frac{\theta_{sp} - \theta}{2\pi} \quad (5)$$

where $\theta_{sp}$ is the value of $\theta$ at the slice plane ($\pi + 2\phi_{max}$ as shown in FIG. 5).

These weights satisfy two conditions 1) the weights assigned to complementary points sum to one, and 2) the weight for each point of the complementary pair is proportional to its relative distance from the slice plane.

Half scan weights must be chosen so that the weights assigned to combined zones of redundant data equal the weight assigned to zones of non-redundant data. Further, the half scan weights assigned to complementary data points in opposing half scans must be equal so that the interpolation is not biased toward one half scan over the other by the half scan weights.

The following half scan weights as functions of $\theta$ and $\phi$ may be used:

$$ha_{1,7} = 3x_1^2 - 2x_1^3 \text{ where } x_1 = \frac{\theta}{2(\phi_{max} - \phi)} \quad (6)$$

$$ha_{2,8} = 3x_2^2 - 2x_2^3 \text{ where } x_2 = \frac{4\phi_{max} - \theta}{2(\phi_{max} + \phi)} \quad (7)$$

$$ha_{2,5} = 1 - ha_{2,8} \quad (8)$$

$$ha_{3,6} = ha_{6,3} = 1 \quad (9)$$

$$ha_{4,7} = 3x_4^2 - 2x_4^3 \text{ where } x_4 = \frac{\theta_{sp} - \theta}{2(\phi_{max} - \phi)} \quad (10)$$

$$ha_{5,2} = 3x_5^2 - 2x_5^3 \text{ where } x_5 = \frac{\theta - \theta_{sp}}{2(\phi_{max} - \phi)} \quad (11)$$

$$ha_{7,1} = 3x_7^2 - 2x_7^3 \text{ where } x_7 = \frac{\theta - 2\pi}{2(\phi_{max} - \phi)} \quad (12)$$

$$ha_{7,4} = 1 - ha_{7,1} \quad (13)$$

$$ha_{8,2} = 3x_8^2 - 2x_8^3 \text{ where } x_8 = \frac{2\theta_{sp} - \theta}{2(\phi_{max} + \phi)} \quad (14)$$

The cubic function forming the basis of these half scan weighting is chosen to have a slope of zero at the edges of zones being weighted and hence to reduce any half scan weighting induced discontinuities.

It will be understood from this description that other half scan weighting functions may be used including a binary weighing function that applies a weight of zero to one zone of each pair of redundant data within a complementary set of data, effectively discarding the redundant data. In a second embodiment, therefore, the half scan weighting of zones 1 and 8 may be mad equal to zero and the half scan weights of regions 2 through 7 may be made equal to one.

Figure 6A:
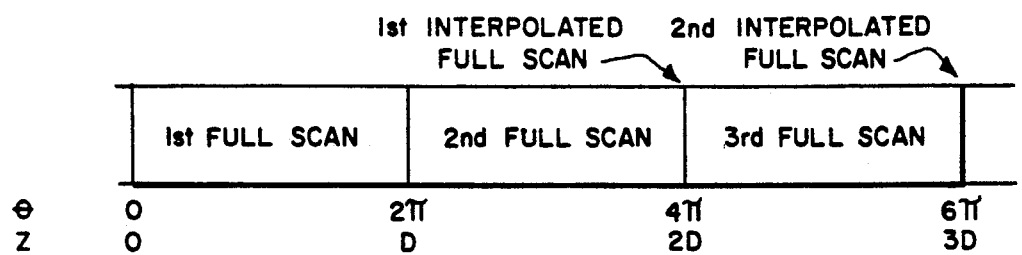
FIG. 6(a) is a graphical representation of the acquisition of helical full scans.

Referring to FIGS. 6(a), a typical helical full scan image acquisition, as is well known, may acquire full tomographic projection sets every $2\pi$ radians of gantry rotation while the imaged object moves distance D which may but need not be equal to the slice thickness. After a first and second full scan have been acquired, an interpolated full scan at the slice plane may be derived from the first and second full scans. Thereafter, an additional interpolated full scan may be calculated after every additional consecutive full scan.

Figure 6B:
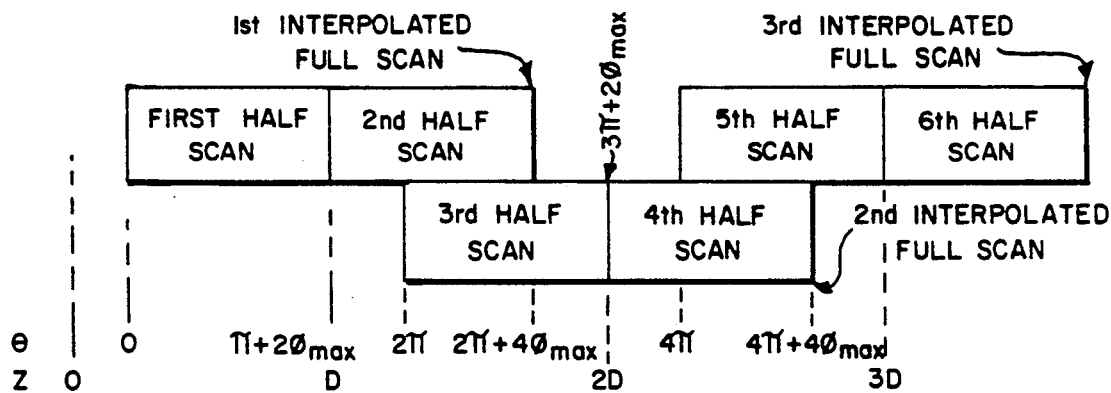
FIG. 6(b) is a graphical representation of the acquisition of helical half scans according to a first embodiment which reduces the z-axis distance and time over which the projection data for the interpolated tomographic projection set is acquired.

Referring to FIG. 6(b), a first method of helical half scan image acquisition acquires a half scan every $\pi + 2\phi_{max}$ radians of gantry rotation which is less than the $2\pi$ radians of gantry rotation required for full scans, while the imaged object moves an equally reduced distance along the z-axis over a shorter period of time. For example, for a fan beam angle of 45°, a half scan may be acquired in only 63% of the distance and time required for a full scan. Reducing the distance from the slice plane over which the scan is acquired improves the accuracy of the interpolation to the slice plane. Reducing the time required for the scan can reduce patient motion image artifacts.

Figure 6C:
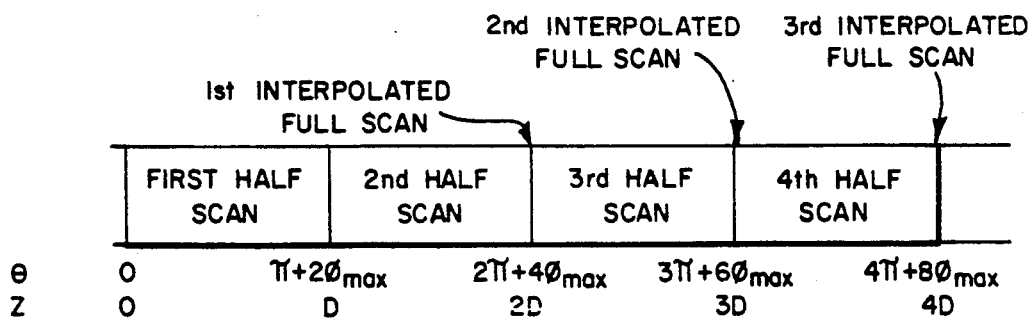
FIG. 6(c) is a graphical representation of the acquisition of helical half scans according to another embodiment which reduces the time during which the projection data for the interpolated tomographic projection set is acquired.

Referring to FIG. 6(c), a second method of helical half scan image acquisition increases the scanning pitch such that the imaged object moves the slice thickness D during each half scan of $\pi + 2\phi_{max}$ of gantry rotation. The distance along the z-axis over which the half scan is acquired is not reduced over that required for a full scan, however, each successive half scan follows immediately after the previous half scan thus shortening the time required to obtain a slice series of consecutive slices.

In both of the above methods the second scan may be reconstructed at any rotation after the first image, so that images can be obtained at any small displacement in z from the first image. A set of images which are separated by a distance in z smaller than the slice thickness is useful for reformation and three dimensional display. These images are obtained with less dose than required by single slice scanning.

Many modifications and variations of the preferred embodiment which will still be within the spirit and scope of the invention will be apparent to those with ordinary skill in the art. For example, other interpolation methods than linear interpolation may be used including those using data from additional half scans before and after the first and second half scans and using higher order interpolation methods. Further, as mentioned, other half scan weighting functions observing the principles described herein may be used. It also should be noted that the half scan reconstruction method is applicable to data sets having projections acquired over greater than 180° plus the angle of the fan beam provided that that the data set is properly weighted, per a half scan weighting function, prior to reconstruction. Generally, this half scan weighting function requires that the sum of the combined weights for any redundant data points, per equation 1, add to the weight a non-redundant data points.

We claim:

1. A method of producing a tomographic image of an image object from data acquired in a helical scan, the data comprising a series of fan beam projections at a plurality of gantry angles $\theta$ about a z axis, the fan beam projections subtending an angle $2\phi_{max}$ within an imaging plane, comprising the steps of:
    a) identifying a slice plane $z_{sp}$ relative to the imaged object and parallel to the imaging plane;
    b) moving the imaged object along the z-axis and rotating the gantry so that the imaging plane crosses the slice plane at a gantry angle of $\theta_O$;
    c) acquiring a first half scan data set prior to the imaging plane crossing the slice plane;
    d) acquiring a second half scan data set subsequent to the imaging plan crossing the slice plane; and
    e) interpolating and reconstructing a tomographic image at the slice plane from the first and second half scans.

2. The method of claim 1 wherein the first half scan data set is acquired of $\theta$ such that $\theta_O - \pi - 2\phi_{max} < \theta < \theta_O$ and the second half scan data set is acquired for $\theta$ such that $\theta_O < \theta < \theta_O + \pi + 2\phi_{max}$.

3. The method of claim 1 wherein the first half scan data set is acquired of $\theta$ such that $\theta_O - \alpha < \theta < \theta_O$ and the second half scan data set is acquired for $\theta$ such that $\theta_O < \theta < \theta_O + \alpha$ where $\alpha$ is less than $2\pi$ but not less than $\pi + 2\phi_{max}$.

4. The method of claim 3 where the half scan weighting function is constant within zones of non-redundant data and varies with angles $\theta$ according to a function $f(x) = 3x^2 - 2x^3$ in zones of redundant data where $x$ is a variable that varies linearly as a function of angles $\theta$ between zero and 1 in zones of redundant data.

5. The method of claim 1 where the tomographic image is interpolated and reconstructed from the first and second half scan data sets by:
    applying a half scan weighting function to the data in the first and second half scan data sets;
    applying a helical scan weighting function to the data in the first and second half scan data sets; and
    reconstructing the first and second weighted half scan data sets.

6. The method of claim 5 including the step of summing the data of the weighted first and second half scan data sets before reconstructing the first and second weighted half scan data sets.

7. The method of claim 5 including the step of combining the weighted first and second half scan data sets into a larger data set before reconstruction.

8. The method of claim 5 where the half scan weighting function is such that the sum of the weights assigned to redundant data within a half scan is equal to the weight assigned to non-redundant data within the half scan and corresponding data between half scans are assigned the same half scan weights.

9. The method of claim 5 where the half scan weighting function is one of two binary values.

10. The method of claim 9 wherein one binary value is zero.

11. A method of producing a series of tomographic images of an imaged object, separated by slice thickness D, from data acquired in a helical scan, the data comprising a series of fan beam projections within an imaging plane at a plurality of gantry angles $\theta$ about a z axis, comprising the steps of:
    a) identifying a slice plane relative to the imaged object;
    b) moving the imaged object along the z-axis and rotating the gantry so that the imaging plane crosses the slice plane;
    c) acquiring a first half scan of projection data prior to the imaging plane crossing the slice plane;
    d) acquiring a second half scan of projection data subsequent to the imaging plane crossing the slice plane;
    e) moving the imaged object so that the imaged object is moved D along the z-axis during each half scan; and
    f) interpolating and reconstructing a tomographic image at the slice plane from the first and second half scans.

12. A method of producing a series of tomographic images of an imaged object, separated by slice thickness D, from data acquired in a helical scan, the data comprising a series of fan beam projections within an imaging plane at a plurality of gantry angles $\theta$ about a z axis, comprising the steps of:
    a) identifying a slice plane relative to the imaged object;
    b) moving the imaged object along the z-axis and rotating the gantry so that the imaging plane crosses the slice plane and so that the imaged object is moved D along the z-axis during each $2\pi$ of gantry rotation;
    c) acquiring a first half scan of projection data prior to the imaging plane crossing the slice plane;
    d) acquiring a second half scan of projection data subsequent to the imaging plane crossing the slice plane; and
    e) interpolating and reconstructing a tomographic image at the slice plane from the first and second half scans.

* * * * *